US007913535B2

(12) United States Patent
Richardson (10) Patent No.: US 7,913,535 B2
(45) Date of Patent: Mar. 29, 2011

(54) APPARATUS AND METHODS FOR DILUTION (75) Inventor: Grant Stuart Richardson, Salisbury (GB)

(73) Assignee: The Secretary of State for Defence in Her Britannic Majesty's Government of the United Kingdom of Great Britain and Northern Ireland (GB)

( * ) Notice: Subject to any disclaimer, the term of this patent is extended or adjusted under 35 U.S.C. 154(b) by 313 days.

(21) Appl. No.: 12/066,660

(22) PCT Filed: Sep. 15, 2006

(86) PCT No.: PCT/GB2006/003437
§ 371 (c)(1),
(2), (4) Date: Mar. 13, 2008

(87) PCT Pub. No.: WO2007/031772
PCT Pub. Date: Mar. 22, 2007

(65) Prior Publication Data
US 2008/0202196 A1    Aug. 28, 2008

(30) Foreign Application Priority Data
Sep. 15, 2005  (GB) .................................. 0518808.1

(51) Int. Cl.
*G01N 31/00* (2006.01)
(52) U.S. Cl. ....................................................... 73/1.06
(58) Field of Classification Search .................... 73/1.06
See application file for complete search history.

(56) References Cited

U.S. PATENT DOCUMENTS

| 4,036,253 | A | | 7/1977 | Fegan et al. |
| 4,619,136 | A | * | 10/1986 | Ortiz ................................. 73/38 |
| 4,974,453 | A | | 12/1990 | Hohorst |
| 5,094,779 | A | | 3/1992 | Carlon et al. |
| 5,509,292 | A | * | 4/1996 | d'Appollonia et al. ........ 73/1.06 |
| 5,661,225 | A | | 8/1997 | Ridgeway et al. |
| 5,907,108 | A | | 5/1999 | Garcia-Rubio et al. |
| 6,125,845 | A | | 10/2000 | Halvorsen et al. |
| 2002/0166390 | A1 | | 11/2002 | Graze, Jr. |
| 2002/0190866 | A1 | * | 12/2002 | Richardson .................. 340/632 |

FOREIGN PATENT DOCUMENTS

| EP | 0519783 | 12/1992 |
| GB | 2259982 | 3/1993 |
| GB | 2294761 | 5/1996 |
| GB | 2335037 | 9/1999 |
| WO | WO 01/43827 | 6/2001 |
| WO | WO 2004/072603 | * 8/2004 |

* cited by examiner

*Primary Examiner* — Hezron Williams
*Assistant Examiner* — Nathaniel Kolb
(74) *Attorney, Agent, or Firm* — Dean W. Russell; Kristin M. Crall; Kilpatrick Townsend & Stockton LLP (57) ABSTRACT

Self-calibrating apparatus and methods for dilution of an analyte-containing fluid, and in particular for dilution of analyte concentrations beyond the normal measurement range of a detector, without the requirement for other detectors. The apparatus is preferably a respirator test system for determining respirator mask fit in the presence of high aerosol challenge concentrations.

11 Claims, 5 Drawing Sheets

APPARATUS AND METHODS FOR DILUTION

CROSS REFERENCE TO RELATED APPLICATIONS

This application is the United States national phase of International Application No. PCT/GB2006/003437 filed on Sep. 15, 2006 and published in English on Mar. 22, 2007 as International Publication No. WO 2007/031772 A1, which application claims priority to Great Britain Patent Application No. 0518808.1 filed on Sep. 15, 2005, the contents of which are incorporated herein by reference.

The present invention is generally concerned with apparatus and methods for dilution. It is particularly, although not exclusively, directed to a method and apparatus suitable for testing respirators.

Improvements in, for example, respirator mask fit mean that known aerosol respirator test systems may now be unable to accurately determine the high level of protection afforded by a respirator. The particle counters employed by such systems are unable to resolve the high aerosol challenge concentrations necessary due to co-incident counting effects. As such, challenge concentrations are limited and consequentially measurement accuracy is reduced by an inability to distinguish particle ingress to the mask over in-mask particle generation.

One approach to the problem of determining high aerosol challenge concentrations in such systems relies on dilution by a known factor so that the particle count falls within the reliable counting range of the particle counter and can be related to the original challenge concentration. However, dilution apparatus developed for the purpose generally rely on mixing known amounts of particles with known volumes of clean air. Such apparatus are inherently unreliable in that over time factors such as particle deposing lead to changes in the dilution.

The present invention generally seeks to overcome these problems by providing dilution apparatus comprising calibration means.

Accordingly, in a first aspect, the present invention provides apparatus for determining the dilution factor of a fluid dilution means, comprising means providing for flow of an analyte-containing fluid, first and second dilution means and detection means for the analyte in which the means providing for flow is arranged such that the output of the first dilution means is directed to the second dilution means and the detection means is arrangeable to determine the concentration of analyte in the output of the first dilution means and in the output of the second dilution means.

The apparatus may be made suitable for a wide range of analyte-containing fluids. However, in a preferred embodiment the apparatus is suitable for dilution of particle aerosols.

Those skilled in the art will appreciate that in one embodiment the apparatus of the present invention determines the dilution offered by the second dilution means and that the first dilution means merely brings the amount of analyte in the input of the second dilution means to a level accurately determinable by a single detector. The extent of dilution offered by the first dilution means is not otherwise important and, in particular, need not be known.

The dilution factor of the second dilution means is calculable as the ratio of the concentration of the analyte in the output of the first dilution means, which is the input to the second dilution means, over the concentration of analyte in the output of the second dilution means.

Those skilled in the art will appreciate that the apparatus is not restricted to two dilution means, and an apparatus comprising multiple dilution means in series, whereupon the relationship between any first and second dilution means is upheld, is also provided.

The apparatus is not limited to any one means providing flow or first and second dilution means. However, in a preferred embodiment, the first and second dilution means are also comprised in the means providing for flow.

In this embodiment, the first and second dilution means may each comprise venturi pumps whereby the vacuum arm of the first pump is in communication with an analyte-containing fluid inlet means and the vacuum arm of the second pump is in communication with the output arm of the first dilution means. The venturi pumps are driven by a flow of a clean fluid providing for dilution of the analyte-containing fluid.

In some embodiments, the first and/or second dilution means may each comprise more than one venturi pump whereby to control the extent of dilution of the analyte-containing fluid.

The first and/or second dilution means may, however, also comprise flow control means for restricting the intake of analyte-containing fluid. Preferably, the flow control means comprises a one-piece flow constriction member defining one or more apertures for access to a through-channel therein. The constriction member is connectable to the vacuum arm of the venturi pump.

Most preferably, the apertures are formed by laser-cutting and have diameter between 10 and 1000 micron, in particular, 10 to 300 micron. The selection of aperture size is made having regard to the desired extent of dilution.

The preferred control flow means are particularly suitable for aerosols comprising particles in that they are much less prone to clogging than, say, needle valves, and can be removed for easy cleaning.

Enhanced accuracy of measurement can be assured through the employment of a mass flow controller (MFC) to meter the fluid supply to each dilution means (i.e. for a venturi pump, the positive fluid driving the positive arm of the venturi).

The detection means may be arrangeable such that a single detector can alternately determine the concentration of analyte in the output of the first dilution means and the concentration of analyte in the output of the second dilution means.

In a preferred embodiment, the detection means comprise a portable particle counter commercially available under the trade name Portacount. The counter which includes pump and valve means, is able to sample one or more air flows and display the number of particles in the sample per unit volume ($n/cm^3$).

The apparatus may, alternatively, comprise a detector suitable to analytes other than particles. The detection means may, in particular, comprise a flame photometer for determining the concentration of a specific analyte (e.g. sodium chloride) or gas chromatography for a vapour.

It will be apparent that the calibrated second dilution means may subsequently be used in independent dilution apparatus for the determination of the concentration of an analyte in a fluid. However, the apparatus of the present invention may be adapted for that purpose.

In a second aspect, therefore, the present invention provides apparatus for determining the concentration of an analyte in a fluid, in which apparatus according to the first aspect is adapted by switching means whereby, in a first mode, the means providing flow is operable to direct the analyte-containing fluid to the second dilution means via the first dilution means and the detection means is operable to determine the concentration of analyte in both the output of the first and second dilution means and in a second mode the means providing flow is operable to direct analyte-containing fluid directly to the second dilution means and the detection means is operable to determine the concentration of analyte in the output of the second dilution means.

Those skilled in the art will appreciate that the apparatus offers calibration of the second dilution means during the first mode of operation and determination of the amount of analyte in a fluid during the second mode of operation.

In a preferred embodiment the switching means provides that in the first mode, the detection means alternately determine the concentration of analyte in the output of the first dilution means and the concentration of analyte in the output of the second dilution means.

Alternatively, the switching means may be such that the detection means determines the concentration of analyte in the combined output of the first and second dilution means. The dilution factor of the second dilution means is then derivable from the difference in the amount of analyte in the combined output of the first mode and the amount of analyte in the output of the second dilution means during the second mode.

The concentration of analyte in the fluid is calculable as the product of the concentration of analyte in the output of the second dilution means during the second mode and the dilution factor.

Suitable switching means comprise simple valve arrangements for the detection means and/or means providing flow. Suitable valves include pinch, solenoid or pneumatic valves.

It is preferred that the means providing flow and the switching means define a substantially similar path length for the analyte-containing fluid in each mode whereby to minimise distortion of the dilution factor between modes on account of differing loss of aerosol. In addition, aerosol loss is minimised by the use of short and straight sections in the means for providing flow.

Apparatus according to the second aspect of the invention is especially useful where it is desired to determine the concentration of aerosols which cause dilution factors to change over time. Such apparatus is appropriate for the determination of the effectiveness of a physical barrier, such as a respirator, by aerosol challenge.

Accordingly, in a third aspect the present invention provides a respirator test system including apparatus according to the second aspect adapted such that the fluid inlet means communicates with an analyte-containing, breathable gas ambient to the respirator and the detection means is operable in the second mode to also determine the concentration of the analyte within the respirator.

Of course, the respirator test system may also comprise such conventional features as a test enclosure and a compressor and fan arrangement for dispersal of an aerosol within the enclosure. The compressor may also drive the venturi pump of the first and/or second dilution means.

In a preferred embodiment, the switching means provides that, during the second mode, the detection means samples the gas within the respirator mask. The switching means may, in particular, provide that the detection means alternately determines the amount of analyte in the output of the second dilution means and the amount of analyte in the respirator mask.

The respirator test system may, in particular, be adapted to minimise distortion of dilution factor between operating modes of the apparatus by providing that the flow means and the switching means are collocated in the test enclosure.

The protection factor of the respirator mask, which is an indicator of respirator mask fit, is derivable from the ratio of the concentration of the analyte in the gas ambient to the respirator over the concentration of analyte in the respirator mask.

In a fourth aspect, the present invention provides a method for determining the dilution factor of a fluid dilution means comprising
i) providing for flow of an analyte-containing fluid through a first dilution means and thence to a second dilution means;
ii) determining the concentration of analyte in the output of the first dilution means; and
iii) determining the concentration of analyte in the output of the second dilution means.

The dilution factor of the second dilution means may be derived from the ratio of the concentration of analyte in the output of the first dilution means over the conception of analyte in the output of the second dilution means.

Those skilled in the art will appreciate that the output of the first dilution means will be an identical concentration of analyte to the input of the second dilution means, irrespective of whether any other means, other than detection means, is provided between the first and second dilution means.

Preferred features of the method will be apparent from preferred apparatus according to the first aspect of the invention.

Those skilled in the art will further appreciate that apparatus according to the first aspect, in which the dilution factor is known or has first been calculated, is suitable for determining the accuracy and calibration of the analyte detection means. The apparatus is easily modified to substitute analyte detection means.

In a fifth aspect, therefore, the present invention provides a method for determining the accuracy and calibration of analyte detection means comprising
i) providing for flow of an analyte-containing fluid through a first dilution means and thence to a second dilution means, the dilation factor of which is known;
ii) determining the concentration of analyte in the output of the first dilution means; and
iii) determining the concentration of analyte in the output of the second dilution means.

The accuracy of analyte detection means may be derived from a comparison of the dilution factor of the second dilution means with the ratio of the concentration of analyte in the output of the first dilution means over the concentration of analyte in the output of the second dilution means.

Those skilled in the art will appreciate that calibration of analyte detection means is enabled in apparatus of the first aspect comprising multiple dilution means in series, and whereupon the relationship between any first and second dilution means is upheld. Calibration is thereby derived from the theoretical concentration of analyte in the output of each second dilution means, which is easily calculable from the dilution factor of each second dilution means.

Preferred features of the method will be apparent from preferred apparatus according to the first aspect of the invention.

In a sixth aspect the present invention provides a method for determining the concentration of an analyte in a fluid in which the method of the fourth aspect additionally comprises
iv) providing for flow of the analyte-containing fluid through the second dilution means alone; and
v) determining the concentration of analyte in the output of the second dilution means.

The concentration of analyte in the fluid is derivable from the product of the amount of analyte as determined in v) and the dilution factor of the second dilution means.

Preferred features of the method will be apparent from preferred apparatus according to the second aspect of the invention.

In a seventh aspect the present invention provides a method for determining respirator mask fit comprising i) performing the method of the sixth aspect of the invention whereby to determine the concentration of analyte in a fluid ambient to the respirator; and
ii) determining the concentration of analyte in the respirator mask.

The aforementioned methods are not limited by a requirement for particular detection means or analyte. Preferably, however, the methods are performed on a particle aerosol using a single particle counter.

The method of the seventh aspect may, in particular, use aerosols comprising a breathable gas, such as air, and sodium chloride or smoke generated from rapid heating of glycerol/water mixtures. However, the method may also use aerosols containing Shell Ondina oil.

The protection factor of the respirator mask, which is an indicator of respirator mask fit, is derivable from the ratio of the concentration of the analyte in the gas ambient to the respirator over the concentration of analyte the respirator mask.

Other preferred features of the method will be apparent from preferred apparatus according to the third aspect of the invention.

In an eighth aspect, the present invention provides a method for producing mixtures of gases and aerosols or other analyte-containing fluids in well-defined concentrations by the dilution of such materials used at high concentrations as the feedstock for the apparatus of the present invention. Once the dilution factor for a particular embodiment of the apparatus has been obtained (as explained previously) and given a known starting concentration, the apparatus can be readily used to provide any desired degree of dilution, particularly by use of a number of dilution means in series. It should also be noted that the gas which is used to drive the dilution means (such as a venturi pump) is not restricted to air but can be any suitable gas such as nitrogen or other fluid, e.g. water vapour.

Such a system may be employed to provide a convenient means of generating calibrated concentrations of gases which may be used subsequently to calibrate the response of equipments such as mass spectrometers or gas chromatographs.

In some circumstances specific stoichiometric gas mixtures are required (e.g. $CO_2$-laser gas mix or for experimental reactions) and such mixtures can be produced by use of the apparatus of the present invention, i.e. mixtures of gases in specified proportions can be obtained where the proportions are determined by the respective flows and orifice sizes of the requisite number of dilution means as will be readily apparent to the skilled person.

In a ninth aspect, the present invention provides a computer programme for performing one or more of the methods of the present invention. The programme may, in particular, provide for the calculation and display of dilution factors.

In a preferred embodiment the computer programme is adapted for use with a respirator test system according to the third aspect of the present invention. In this embodiment, the computer programme may also be operative to enable control of the concentration of the analyte ambient to the respirator mask and to calculate and display protection factors.

The present invention is particularly advantageous in that it enables efficient, rapid and automated calibration of fluid dilution means for analyte concentrations beyond the normal measurement range of an available detector without the requirement for other detectors. The use of the apparatus as internal calibration means avoids uncertainty in dilution apparatus. In addition, the venturi pump and flow control means provides aerosol dilution factors of between 2 and 500,000 which, for a given flow rate, are consistent over a broad range of high aerosol starting concentrations. Single venturi pumps comprising apertures formed by laser-cutting provide aerosol dilution factors in excess of 100, and dilution factors of >1000 are easily obtainable for gaseous analytes.

Methods and apparatus according to the present invention are now described with reference to the following embodiments and the accompanying drawings in which FIGS. 1a) and 1b) are schematics showing a respirator test system according to the present invention in a) calibration mode and b) test mode.

Figure 1A:
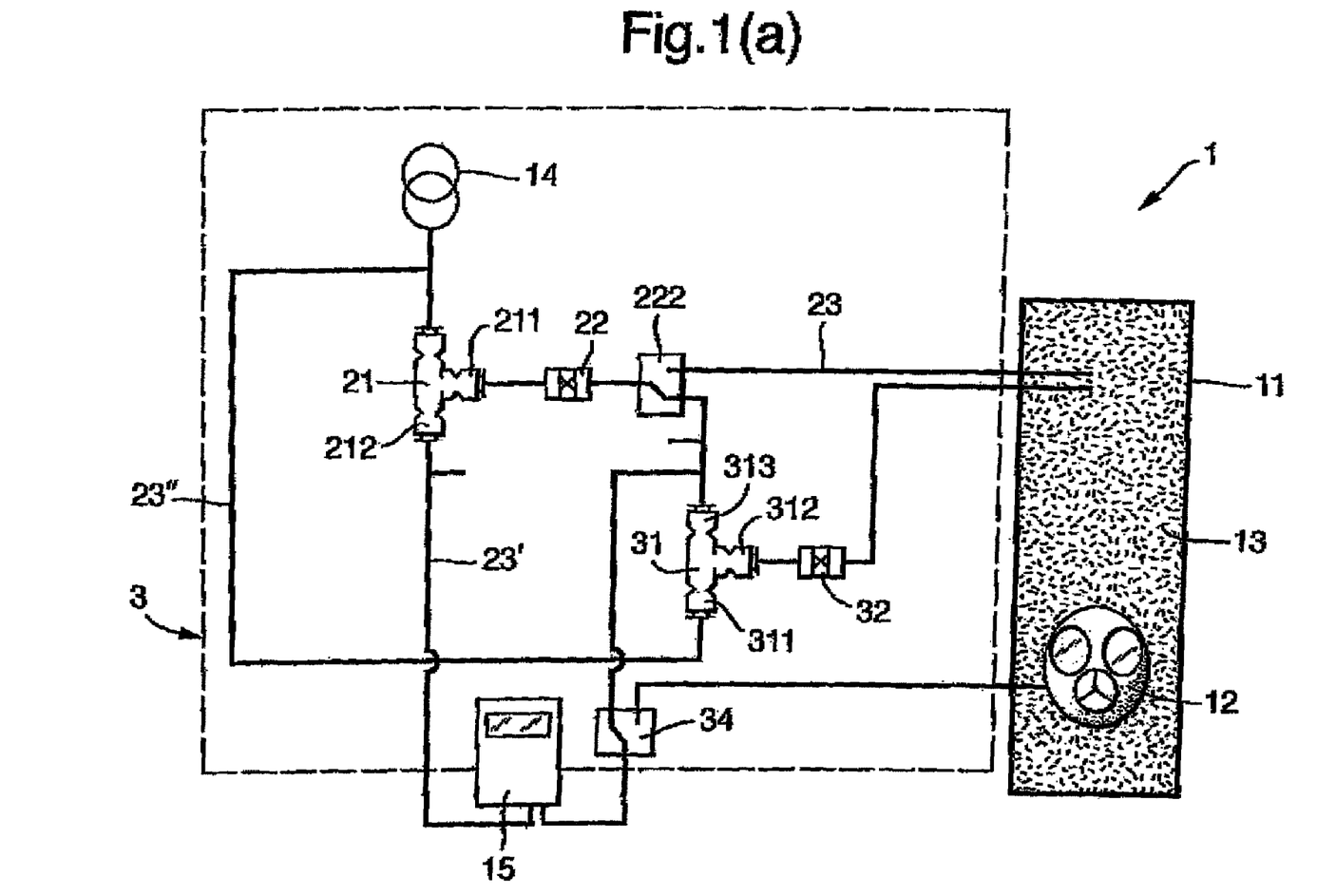
Figure 1B:
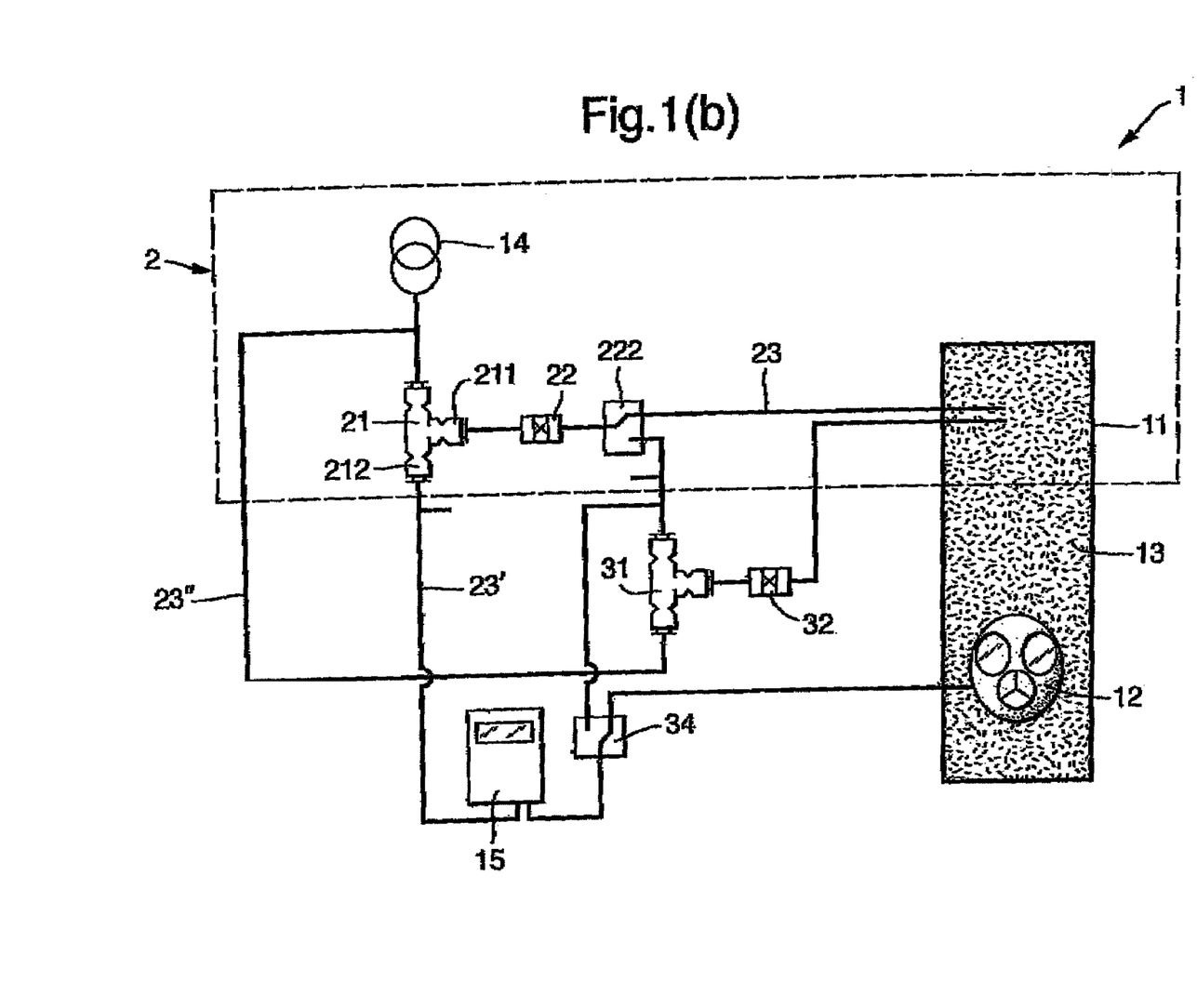

Referring now to FIGS. 1a) and b), a respirator test system, generally designated 1, comprises a dilution rig, generally designate 2, a calibration rig, generally designated 3, and a test housing 11 enclosing a respirator mask 12 within an aerosol dispersion 13 of particles in air.

The dilution rig 2 comprises a single venturi pump 21 which is driven by a rotary vane air pump 14. Air from the pump 14 is fed through a filter (not shown) to ensure that it is clean before being used in the apparatus. The vacuum arm 211 of venturi pump 21, which is connectable by way of sample tubing 23 and valve arrangement 222 to the test housing 11, includes a hollow finger providing a circular aperture of 100 micron at its distal end (shown as 22). The output arm 212 of the venturi pump 21 is connected by way of sample tubing 23' to a Portacount™ particle counter 15. A vent is provided to the output tubing for escape of excess air.

The self-calibration rig, generally designated 3 (FIG. 1a), former comprises a single venturi pump 31 and tubing 23" enabling connection of the rotary vane pump 14 to the input arm 311 of the venturi pump 31. The vacuum arm 312 of venturi pump 31, is connected via hollow finger (32, similar to hollow finger 22), to the test housing 11. The output arm 313 of venturi pump 31 is connectable to the vacuum arm 211 of the venturi pump 21 of the dilution rig by two-way valve 222.

The output tubing from pump 31 further includes a junction which, together with a second two-way valve (34) enables connection of the output from 31 to particle counter 15. Alternatively, by activation of valve 34, counter 15 can instead be connected to the respirator mask 12. The output tubing also includes a vent for escape of excess aerosol.

The venturi pumps 21 and 31 function continuously to avoid any changes in flow or dilution which may occur upon changing between calibration mode and test mode.

Referring now to FIG. 1a), the system is operable, in self-calibration mode, such that aerosol 13 within the test housing 11 is admitted to the vacuum arm 312 of the venturi pump 31, diluted and fed via the output arm 313 to the vacuum arm 211 of the venturi pump 21.

The particle counter 15 draws alternately upon the diluted aerosol 13 of each of the output of the venturi pump 21 and the output of venturi pump 31 during predetermined periods (for example 5 seconds each). The particle counter 15 determines the concentration of particles in each sampled output as number of particles per unit volume. The dilution factor is obtained simply as the ratio of concentration in the sampled output of venturi pump 31 over the concentration in the sampled output of the venturi pump 21.

To switch from the self-calibration routine to test mode, two-way valves 222 and 34 are actuated so that the venturi pump 31 is by-passed and the particle counter 15 is connected to the interior of the respirator mask 12 (FIG. 1b).

Referring now to FIG. 1b) the apparatus is operable, in test mode, such that aerosol is admitted from the test housing 11 to the vacuum arm 211 where it is diluted and fed to the particle counter 15 via output arm 212. The particle counter 15 alternately draws upon the output of each of the venturi pump 21 and the interior of the respirator mask 12 during predetermined periods. The particle counter 15 determines the concentration of particles as number of particles per unit volume. After correction for the effect of differing time periods, the protection factor of the respirator mask 12 is obtained as the ratio of the product of the average concentration in the output of venturi pump 21 and the dilution factor over the average concentration in the respirator mask 12.

EXAMPLE 1

A broad range of known aerosol challenge concentrations were compared with the dilution effected by the respirator system and the dilution factor obtained by internal calibration. The aerosol challenge comprised smoke generated by rapid heating of glycerol/water mixtures. The rotary vane pump provided a mains pressure of 1000 mbar and the particle counter operated at 0.711 L/min. The results were plotted.

Figure 2:
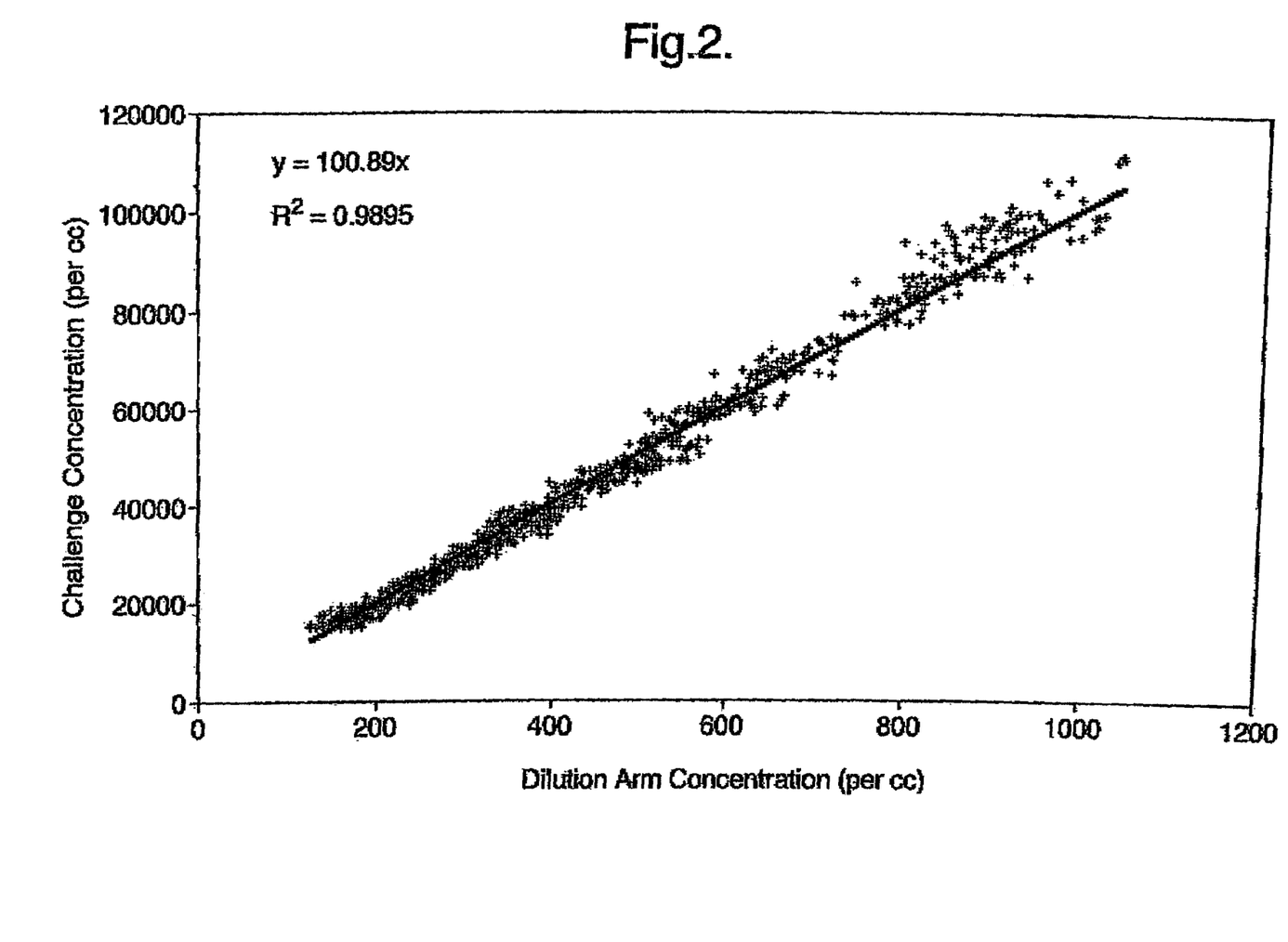
FIG. 2 is a graph showing the relationship between aerosol challenge concentration and the concentration of analyte in the output of the second dilution means.
Figure 3:
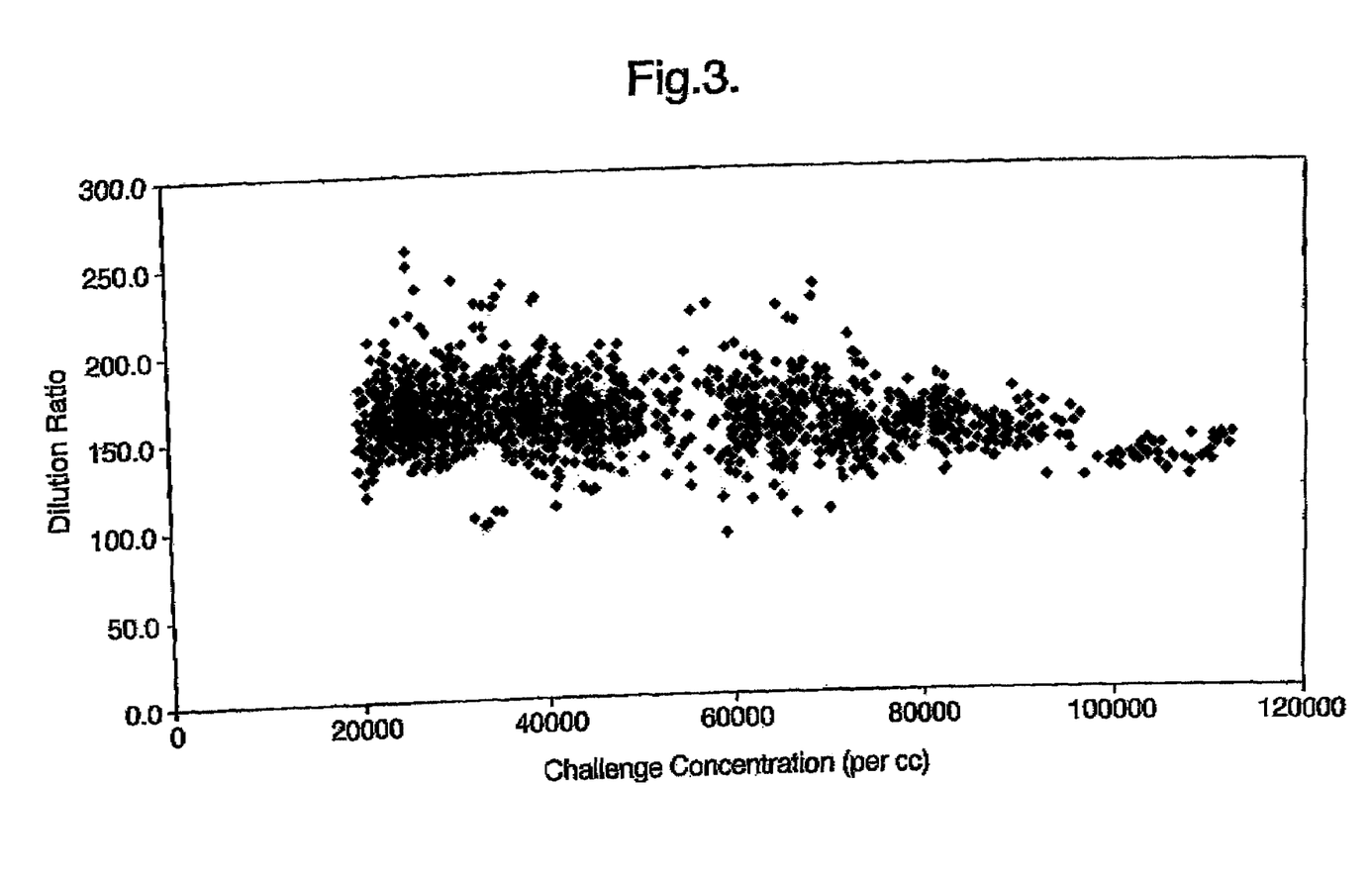
FIG. 3 is a graph showing the relationship between aerosol challenge concentration and the dilution factor of the second dilution means.

As may be seen from FIGS. 2 and 3, the relationship between dilution concentration and high starting challenge concentration is essentially linear and the dilution factor remains roughly constant.

Similar results were obtained at other mains pressures between 500 mbar and 2000 mbar.

In an alternative arrangement a Shell Ondina oil aerosol was generated using a commercially available laskin aerosol generator, aerosol being bled from the compressor, filtered and used to drive both the venture pumps and the pneumatic pinch valves of apparatus of the invention.

Figure 4:
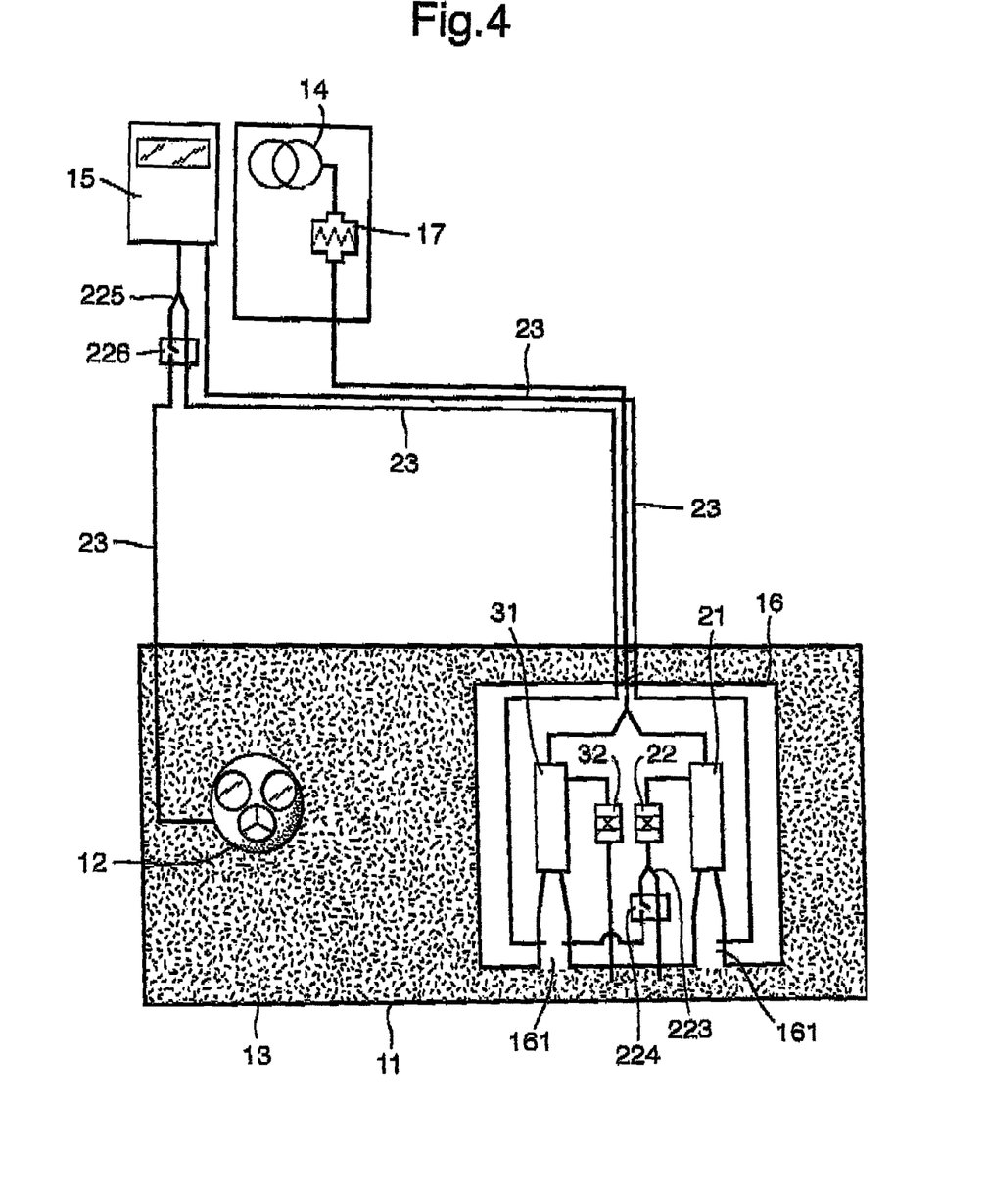
FIG. 4 is a schematic showing a preferred respirator test system according to the present invention.

Referring now to FIG. 4, the respirator test system 1 described above is adapted such it provides a substantially similar flow path for the challenge aerosol in both the test and the calibration mode.

The rotary vane pump 14 and particle counter 15 are arranged outside the test housing 11 whilst the dilution and calibration rigs 2, 3 are provided in a unit 16 within the test housing 11. The unit 16 and test housing 11 provide apertures for connection of the rotary vane pump 14 to both venturi pumps 21, 31 by sample tubing 23 and respective hollow fingers 22, 32. Air from the rotary vane pump is first fed through a paper filter 17 to ensure that it is clean before it enters the apparatus.

The unit also provides parallel exhaust channels 161 for the output of each pump. The exhaust channel 161 for each pump includes an aperture allowing for connection of the particle counter by sample tubing. The exhaust channel for the calibrating pump 31 also includes an opposing aperture allowing connection by sample tubing of its output to the input of the diluting pump 21 in the calibration mode.

The valve arrangement differs from that described above in that the sample tubing connecting the output of the calibrating pump 31 to the input of the diluting pump 21 comprises a Y-piece 223. The remaining limb is connectable to an aperture in the unit 16 providing for intake of the aerosol 13 to the diluting pump 21 in the test mode. The unit 16 also provides an adjacent aperture for the intake of aerosol to the vacuum arm of the calibrating pump 31 in the calibration mode.

A pair of opposing (one open, one dosed) pinch valves 224 enables switching between the calibration and test modes with similar Y-piece/pinch valve combination 225, 226 allowing either the output from pump 31 or the respirator to be connected the particle counter 15 as appropriate.

The unit 16 and, in particular the position of the channels and apertures within it, provide that the dilution and calibration rigs can be laid out so that substantially similar lengths (shown) of sampling tubing 23 are used in each mode. The extent of particle deposition and loss of aerosol is minimal, but also similar in each mode, meaning that the dilution factor does not vary according to mode.

The respirator systems according to the present invention provide consistent dilution over sustained periods of time and, in particular, enable aerosol challenge concentrations beyond the normal range of Portacount™ to be determined in a straightforward manner.

The invention claimed is:

1. A self-calibrating dilution apparatus, comprising means providing for flow of an analyte-containing fluid, first and second dilution means, detection means for the analyte, and switching means, wherein a dilution factor of the second dilution means is unknown, wherein the detection means is a single detector, and wherein the means for providing flow and the switching means are arranged so that in a first mode, the means providing for flow directs output of the first dilution means to the input of the second dilution means, and the detection means alternately determines the concentration of the analyte in the output of the first dilution means and in the output of the second dilution means; and in a second mode, the means providing for flow directs analyte-containing fluid directly to the second dilution means, and the detection means is operable to determine the concentration in the output of the second dilution means.

2. Apparatus according to claim 1, in which the first and second dilution means are comprised in the means providing for flow.

3. Apparatus according to claim 2, in which the first dilution means comprise a venturi pump.

4. Apparatus according to claim 3, in which the second dilution means comprise a venturi pump.

5. Apparatus according to claim 4, in which the first or second or both dilution means comprise flow control means comprising a single-piece constriction member defining one or more apertures for access to a channel defined therein.

6. Apparatus according to claim 5, in which the apertures are formed by laser-cutting.

7. Apparatus according to claim 1, in which the detection means comprise a particle counter, flame photometer or gas chromatograph.

8. A respirator test system comprising apparatus according to claim 1, in which the means providing for flow directs an analyte-containing fluid ambient to the respirator to the first or second or both dilution means and the detection means determines the concentration of analyte within the respirator during the second mode.

9. A method for determining respirator mask fit, comprising (i) arranging for the flow of an analyte-containing fluid ambient to the respirator to a first dilution means and directing the output to a second dilution means of unknown dilution factor;

(ii) determining the concentration of analyte in the output of the first dilution means;
(iii) determining the concentration of analyte in the output of the second dilution means;
(iv) calculating the dilution factor of the second dilution means as the ratio of the concentrations of analyte determined in steps (ii) and (iii);
(v) arranging for the direct flow of the analyte-containing fluid ambient the respirator to the second dilution means;
(vi) determining the concentration of the analyte in the output of the second dilution means;
(vii) calculating the concentration of analyte in the fluid ambient the respirator as the product of the dilution factor and the concentration of analyte determined in step (vi);
(viii) determining the concentration of analyte within the respirator mask; and
(ix) calculating the protection factor of the respirator, as an indicator of respirator mask fit, as the ratio of the concentrations of analyte determined in steps (vii) and (viii)

wherein the determination of the concentration of the analyte in steps (ii), (iii), (v) and (vii) is performed using a single detector.

10. A method according claim 9, in which the analyte comprises particles.

11. A computer readable medium comprising program instructions for performing the method of claim 9.

* * * * *